(12) United States Patent
Goldbach

(10) Patent No.: US 8,295,909 B2
(45) Date of Patent: Oct. 23, 2012

(54) MEDICAL TRACKING SYSTEM WITH INFRARED DATA TRANSFER

(75) Inventor: Günter Goldbach, Forstinning (DE)

(73) Assignee: Brainlab AG, Feldkirchen (DE)

( * ) Notice: Subject to any disclaimer, the term of this patent is extended or adjusted under 35 U.S.C. 154(b) by 1513 days.

(21) Appl. No.: 11/424,372

(22) Filed: Jun. 15, 2006

(65) Prior Publication Data

US 2007/0013783 A1 Jan. 18, 2007

Related U.S. Application Data

(60) Provisional application No. 60/695,179, filed on Jun. 29, 2005.

(30) Foreign Application Priority Data

Jun. 16, 2005 (EP) ..................................... 05012982

(51) Int. Cl.
*A61B 5/05* (2006.01)

(52) U.S. Cl. ......... 600/424; 600/407; 600/429; 600/473

(58) Field of Classification Search ........................ None
See application file for complete search history.

(56) References Cited

U.S. PATENT DOCUMENTS

| | | | |
|---|---|---|---|
| 4,611,291 A | 9/1986 | Hoelscher | |
| 5,528,264 A * | 6/1996 | Kautzer et al. | 345/158 |
| 5,555,120 A * | 9/1996 | Telymonde et al. | 398/111 |
| 5,562,621 A * | 10/1996 | Claude et al. | 604/100.03 |
| 5,572,999 A | 11/1996 | Funda et al. | |
| 5,769,861 A | 6/1998 | Vilsmeier | |
| 5,788,688 A | 8/1998 | Bauer et al. | |
| 5,819,229 A | 10/1998 | Boppe | |
| 6,106,512 A | 8/2000 | Cochran et al. | |
| 6,117,127 A | 9/2000 | Helmreich et al. | |
| 6,120,435 A | 9/2000 | Eino | |
| 6,154,139 A * | 11/2000 | Heller | 340/573.4 |
| 6,161,033 A | 12/2000 | Kuhn | |
| 6,285,742 B1 * | 9/2001 | Haumann et al. | 378/116 |
| 6,471,363 B1 | 10/2002 | Howell et al. | |
| 6,602,185 B1 | 8/2003 | Uchikubo | |
| 6,608,688 B1 * | 8/2003 | Faul et al. | 356/614 |
| 6,642,836 B1 | 11/2003 | Wang et al. | |
| 6,659,939 B2 | 12/2003 | Moll et al. | |
| 6,675,040 B1 | 1/2004 | Cosman | |
| 6,928,490 B1 | 8/2005 | Bucholz et al. | |
| RE39,102 E * | 5/2006 | Schulz et al. | 356/139.03 |
| 7,053,752 B2 * | 5/2006 | Wang et al. | 340/3.54 |
| 7,294,106 B2 * | 11/2007 | Birkenbach et al. | 600/300 |
| 7,501,995 B2 * | 3/2009 | Morita et al. | 345/7 |
| 7,573,439 B2 * | 8/2009 | Lau et al. | 345/7 |
| 7,588,369 B2 * | 9/2009 | Varjonen et al. | 378/191 |
| 7,725,162 B2 * | 5/2010 | Malackowski et al. | 600/424 |
| 7,873,400 B2 * | 1/2011 | Moctezuma De La Barrera et al. | 600/424 |
| 2002/0147455 A1 | 10/2002 | Carson | |

FOREIGN PATENT DOCUMENTS

DE 196 39 615 A1 4/1998
WO 02/19957 A2 3/2002

* cited by examiner

*Primary Examiner* — Long V. Le
*Assistant Examiner* — Bradley Impink
(74) *Attorney, Agent, or Firm* — Renner, Otto, Boisselle & Sklar, LLP

(57) ABSTRACT

A medical tracking and appliance control system includes a medical tracking system having a camera array and an infrared light source, and at least one medical appliance controllable via infrared signals or operative to exchange data via infrared signals. The infrared light source of the medical tracking system is operable to provide wireless control and/or data exchange with the medical appliance.

18 Claims, 1 Drawing Sheet

MEDICAL TRACKING SYSTEM WITH INFRARED DATA TRANSFER

RELATED APPLICATION DATA

This application claims priority of U.S. Provisional Application No. 60/695,179 filed on Jun. 29, 2005, which is incorporated herein by reference in its entirety.

FIELD OF THE INVENTION

The invention relates to the field of medical tracking systems and data transfer between medical appliances.

BACKGROUND OF THE INVENTION

Medical tracking systems are used to track and/or determine the three-dimensional position of instruments or treatment means in a medical work space. In most cases, medical tracking systems comprise two cameras, and such systems may operate using non-visible light, e.g., using infrared light cameras that detect infrared light. The infrared light may be provided by a system-integrated infrared light source, in most cases in the form of short flashes of infrared light. These flashes are reflected by reference reflector means on instruments, patients or treatment means, from which the three-dimensional position of the instruments, patients and/or treatment means can be determined by a camera array (and integrated electronics). Examples of such an infrared tracking system are known from DE 196 39 615 A1 and U.S. Pat. No. 6,351,659 B1, which are hereby incorporated by reference in their entirety.

Many controllable appliances are used in operation theaters, such as, for example, height-adjustable patient couches, audio and video recording appliances or operation lamps, etc. There also is data exchange between appliances in an operating theater, one example of this being the wire transfer of positional data between the medical tracking system and a medical navigation system.

With respect to controlling appliances in an operating theater, this is often realized using infrared remote controls. In operating theaters provided with an infrared tracking system that operates using very intense infrared signals, however, the infrared tracking signals can be superimposed on the control signals of the remote controls and impair the control function. Saturation of the infrared receivers of the controlled appliances also can occur.

SUMMARY OF THE INVENTION

The invention provides a combined system including a medical tracking system that comprises a camera array and an infrared light source, and at least one appliance that is used in a medical setting (e.g., in a treatment and/or examination room and/or setting), in particular a medical appliance. The medical appliance can be controlled using infrared signals and/or can exchange data by means of infrared signals, wherein the infrared light source of the medical tracking system forms at least a part of the system's wireless control unit and/or data exchange unit. In other words, the infrared light source of the medical tracking system can act as a carrier for data signals so as to enable data exchange between the tracking system and the medical appliances. This is advantageous, for example, in that the infrared light source no longer operates as a disrupting factor but rather as a part of the control/data transfer system, and disruptions can therefore be minimized or eliminated. Further, control signals and/or data transfers can be made more secure and more reliable, since the infrared light source of the tracking system is relatively intense. Other advantages are also described below.

The system can include at least one of the following appliances:
- an operation lamp;
- a medical navigation system;
- a medical robot;
- a data or image recording appliance;
- a data or image reproducing appliance;
- a patient couch;
- an operating theater microscope;
- a bi-polar or uni-polar, surgical high-frequency instrument;
- an endoscope;
- an ultrasound device;
- a fluoroscope;
- a laser registration device;
- multiple tracking means;
- automatic supporting or holding devices;
- a ceiling light;
- an audio/video system;
- a thermal mat;
- a printer; or
- any other appliance which can be controlled or can process data in an operating theater.

Controlling operation lamps, for example, can relate to the brightness, focus and/or position of the lamps. Controlling microscopes can influence the focus, zoom, position and/or brightness of the microscope lamp. Surgical high-frequency instruments, for example, can be controlled cutting or coagulation instruments. Light sources can be selected for endoscopes, and their brightness set. Ultrasound appliances can be set with respect to their focus, depth, frequency and/or modes. C-arc fluoroscopes can be set with regard to the dosage, time and/or release. Power and/or timing can be set for laser registration devices, and multiple tracking systems can be set with respect to their synchronization and transfer time. Automatic supporting systems can be controlled with regard to their speed and direction, as can robots, which also can receive positional information and/or mode information.

Recording and playback appliances can receive the typical control commands, as well as data pertaining to what should be recorded. Input and control appliances and/or image output appliances or such appliances in combination (e.g., a touch-sensitive screen) can provide input and output functions and data exchange functions and, thus, also can utilize the control and/or data exchange function. The temperature of thermal mats can be set, and output systems, such as, for example, printers, can be controlled and/or supplied with data. All these functions can be fulfilled using the existing infrared light source.

The system preferably comprises a central processing unit for control and/or data exchange, which may be integrated in one of the medical appliances. Data, for example, can be processed by an available navigation system or a part of the navigation system.

Within the scope of the invention, it is likewise possible to provide a central input unit for control and/or data exchange, as a control console, so to speak. This central input unit preferably is integrated in one of the medical appliances, in particular in the appliance comprising the aforementioned processing unit, and can be a touch-sensitive screen of the navigation system, for example.

In a method for controlling medical appliances and/or for data exchange between medical appliances, an infrared light source of a medical tracking system is used as at least a part of the system's wireless control and/or data exchange unit.

Embodiments of the method include addressing the above-listed appliances using the infrared light source, wherein the term "addressing" includes any data exchange, e.g., exchange of information such as, for example, images, medical or anatomical data, and exchange of control signals.

The control signals and/or data exchange signals can be provided in the signal intervals between the tracking signal outputs of the infrared light source. Furthermore, it is possible to convey and/or output the data exchange signals as an addition to the tracking signal outputs of the infrared light source or instead of the tracking signal outputs.

In accordance with a preferred embodiment of the method, the camera array is controlled such that recording is disabled at times when there are no tracking signal outputs. This avoids the undesired use of control signals or data exchange signals for instrument tracking.

The invention further relates to a program which, when running on a computer or loaded onto a computer, causes the computer to carry out one of the methods described above. The invention also includes a computer program storage medium comprising such a program.

The present invention provides a control and/or data transfer system in which the already existing infrared signal output capability of the tracking system is used to control other infrared-controllable devices by emulating their commands. To this end, it is quite acceptable to halt the normal instrument tracking mode and/or to transmit suitable control commands during internal processing times in which the infrared light signals are not needed for image acquisition. It should be noted that when infrared signals are referred to herein, other types of wireless signal transfer, for example other types that operate using non-visible light, could also be envisaged by persons skilled in the art. In general, it would also be possible to use ultraviolet radiation as a tracking signal and simultaneously as a data exchange signal and/or control signal, for example. Within the scope of the invention, it is advantageous if the power used by the tracking system also is the power for controlling appliances and/or for exchanging data.

All the data provided by the tracking system can be transmitted wirelessly to one or more host devices (e.g., computer, robot, navigation system) using either digital or analog infrared light modulation, without the need for additional wireless transfer systems and devices.

A central control system overcomes the practical problem of having to provide multiple infrared control units in the operating theater to control different devices. Multiple remote controls are no longer needed, and necessary settings can be made to the appliances from the central control unit (e.g., the touch-sensitive screen).

Problems with an interrupted "line of sight", e.g., with offset control paths, as may occur using manual remote controls are eliminated, since the infrared flashes of the tracking system are intense enough to reach substantially every angle in the operation theater, either directly or via sufficiently intense light reflections in the room. As a result, remote controls for the appliances are no longer needed, nor are the batteries used in such remote control devices. Omitting the remote controls and their batteries also makes it much easier to maintain sterility in the operating theater.

The invention enables wireless data transfer to multiple receivers without disruptive cables in the operating theater and with very low integration costs since at least the transmitter, i.e., the infrared light source, is already available. Multiple appliances can be completely integrated in the operating theater without multiple interfaces.

BRIEF DESCRIPTION OF THE DRAWINGS

The forgoing and other embodiments of the invention are hereinafter discussed with reference to the drawings.

DETAILED DESCRIPTION

Figure 1:
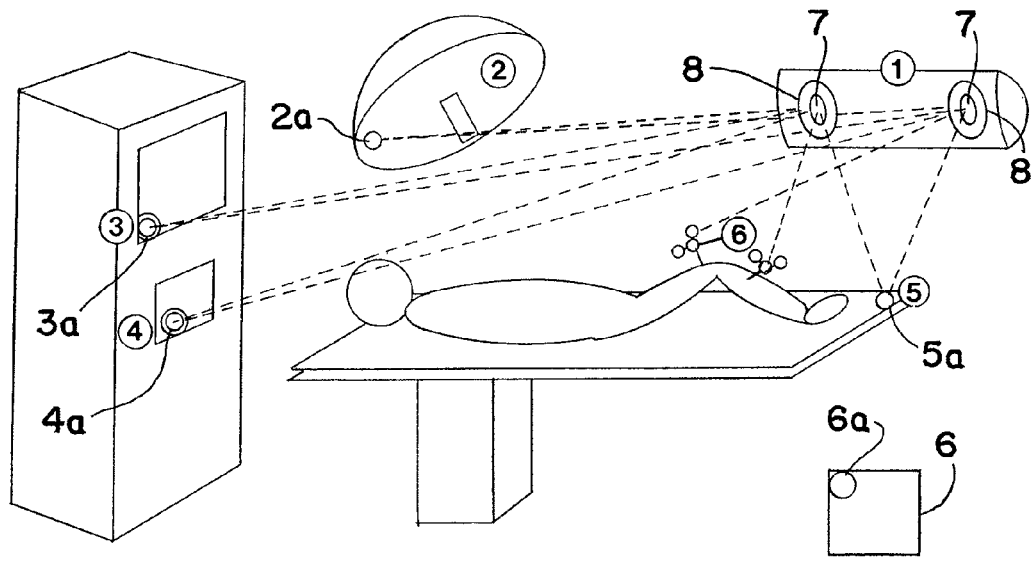
FIG. 1 illustrates an operating theater set up with an exemplary system in accordance with the invention.

FIG. 1 illustrates a medical tracking system 1 that includes two infrared cameras 7 which are surrounded by diode rings 8. The diode rings 8 contain infrared diodes and can emit infrared flashes and/or signals, the reflections of which can be received by the cameras 7 (infrared cameras). In this way, the position of a patient's body part, for example, is conventionally "tracked", i.e., determined and tracked. This conventional tracking, for example, is performed using reference stars 6 that are attached to the patient, such as the patient's leg. Medical instruments or treatment means also can be tracked using such reference stars 6.

Other appliances also are shown in the operating theater setup of FIG. 1, namely a patient couch 5, an operation lamp 2, a navigation system 3 and a recording device (e.g., video/audio) 4. Additional appliances 6, such as a medical robot, data or image recording and/or reproducing appliance, microscope, surgical instrument, endoscope, ultrasound device, fluoroscope, laser registration device, supporting devices, multiple tracking devices, lighting devices, audio/video systems, thermal mats, printers, etc. also can be utilized. These appliances are then likewise controlled using signals provided by the LED rings 8 as infrared signals. In addition, receivers shown as points 2a, 3a, 4a, 5a and 6a are provided on each of the appliances 2, 3, 4, 5 and 6 (which can be the already existing infrared receivers of the appliances). By outputting a signal via the infrared LED ring 8 to the receiver 5a of the couch 5, for example, the height of the couch 5 can be adjusted using its motors (not shown). The operation lamp 2 can be switched to a different mode, made brighter or darker, and/or its focus can be changed. The video/audio recording appliance 4 can be controlled in order to initiate or play back recordings which could be used to support the treatment.

Using the navigation system 3, the tracking system 1 can both exchange control commands and transfer data via the LED rings 8. One example of data transfer is the transmission of the detected positions of reference stars 6 by the tracking system 1 to the navigation system 3. However, control commands also can be transmitted, and on the basis of the navigation system 3, it is possible to implement two-way communications between the tracking system 1 and other devices, such as the medical appliances, for example. The navigation system 3, for example, can comprise a touch-sensitive screen, via which control inputs are possible. The navigation system 3 then transmits these control inputs to the tracking system 1 (e.g., to the cameras or an additional receiver), which in turn relays the control commands via the LED rings 8. Control commands which merely relate to controlling the tracking system 1, e.g., changing variable properties of the tracking system 1 such as camera orientation, also can be transferred from the navigation system 3 to the tracking system 1.

The present invention thus provides an optimal communication system for an operational setup using many existing elements.

Figure 2:
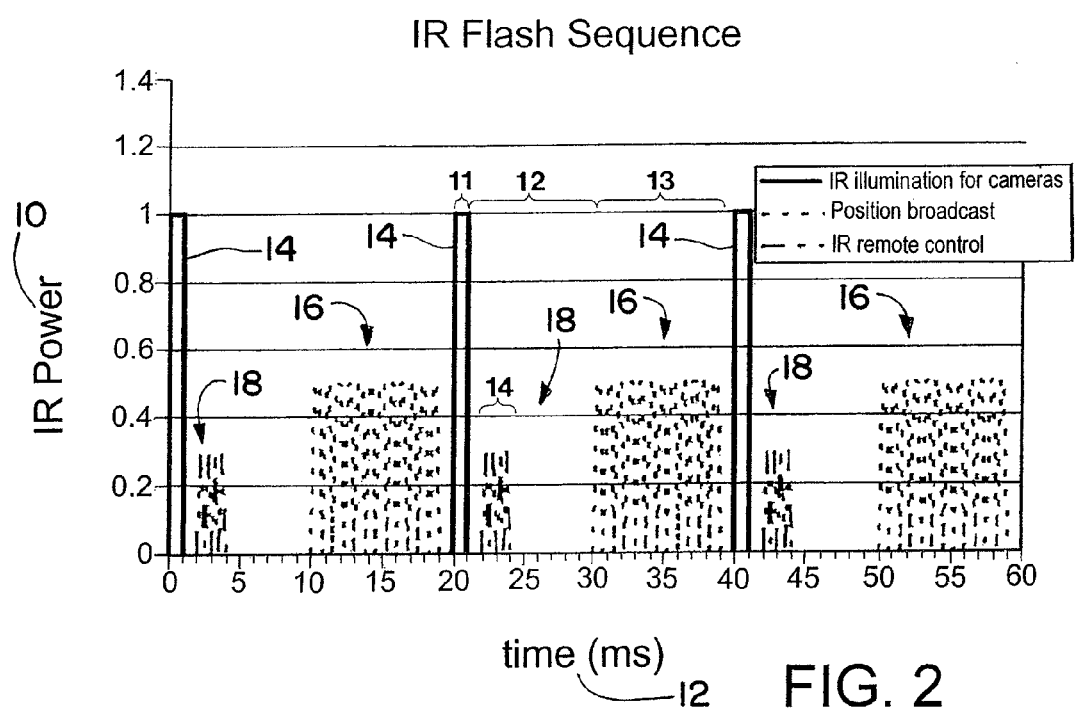
FIG. 2 illustrates a typical infrared signal output sequence for a passive tracking system and/or navigation system (image-guided surgery system).

FIG. 2 represents an exemplary infrared signal output sequence of a passive image-guided surgery system (navigation system). The vertical axis 10 shows the infrared energy, while time in milliseconds is plotted on the horizontal axis 12. The thick lines 14 indicate the infrared signal output for the tracking camera 7, the short-dashed marks 16 relate to the relay of positional information and the dot-and-dash lines 18 show the infrared remote control times and/or control/data exchange times.

In the representation, t1 indicates the image acquisition time. An object of the infrared flashes for a passive tracking systems based on infrared technology is to illuminate the setting of the operating theater with intense infrared light, while the sensors (e.g., cameras 7) acquire the images for detecting marker positions (e.g. marker reference arrays 6 in FIG. 1). Typically, this time interval lasts between a few micro seconds (e.g., 10 μs) and a few milliseconds. In the example of FIG. 2, one millisecond is needed for every 20 millisecond window, which would be the case for a tracking system with 50 images per second.

The time t2 is the image processing time: subsequent to the image acquisition time t1, the image processing system needs a certain time to detect and process the three-dimensional positions.

The time t3 is the data transfer time and/or data relay time: once image processing has been completed, the positional information can be transferred (to the navigation system) using the same infrared emitters (LED rings 8 in FIG. 1), at the same or even a lower energy level than the infrared flashes (t1), using optical data transfer techniques, for example infrared data association (IrDA).

The time t4 remains as a free time for controlling other infrared-controllable appliances. During the image processing time t2, the infrared emitters (LED rings 8 in FIG. 1) can be used to control other nearby appliances, by emulating their infrared remote control protocols.

By using this technique, interference from other infrared remote controls, which would have to be used in the setup together with the infrared illumination of the tracking system, is avoided by time multiplexing (time phase control). The relatively long image processing time can be used as a time frame for controlling other infrared-controllable appliances, since it remains otherwise unused. The data of the navigation system can be relayed to one or more receivers which can also process the tracking information further.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A medical tracking and appliance control system, comprising:

a medical tracking system including a camera array and an infrared light source, the infrared light source configured to provide infrared light in a medical workspace for reflection by trackable markers placed in the medical workspace, and the camera array configured to detect a position of the markers based on the infrared light reflected by the markers;

at least one medical appliance controllable via infrared signals or operative to exchange data via infrared signals; and a controller for controlling the infrared light source of the medical tracking system to provide wireless control and/or data exchange with the at least one medical appliance, said controller configured to time-multiplex light output by the light source into a plurality of time periods, wherein a first time period of the plurality of time periods corresponds to an image acquisition period of the camera array, and a second time period of the plurality of time periods corresponds to at least one of a wireless control period or a data transfer period with the at least one medical appliance.

2. The system according to claim 1, wherein the at least one medical appliance is at least one of an operation lamp, a medical navigation system, a medical robot, a data or image recording appliance, a data or image reproducing appliance, patient couch, an operating theater microscope, a bi-polar or uni-polar surgical high-frequency instrument, an endoscope, an ultrasound device, a fluoroscope, a laser registration device, multiple tracking means, automatic supporting or holding devices, a ceiling light, an audio/video system, a thermal mat, or a printer.

3. The system according to claim 1, further comprising a central processing unit for control and/or data exchange.

4. The system according to claim 3, wherein the central processing unit is integrated in the at least one medical appliance.

5. The system according to claim 1, further comprising a central input unit for control and/or data exchange.

6. The system according to claim 5, wherein the central input unit is integrated in the at least one medical appliance.

7. The system according to claim 6, wherein the at least one medical appliance comprises a processing unit.

8. The system according to claim 1, wherein the infrared light source is integrated with the camera array.

9. The system according to claim 1, wherein the controller is configured to time displace tracking signals for tracking an object relative to control signals for controlling the at least one medical appliance or data signals exchanged with the at least one medical appliance, wherein the tracking signals are different from the control signals and the data signals.

10. A method for controlling at least one medical appliance in a medical setting or for data exchange between the at least one medical appliance and other systems, said controlling and data exchange performed using medical tracking system that includes an infrared light source configured to provide infrared light in a medical workspace for reflection by passive markers placed in the medical workspace, comprising using the infrared light source of the medical tracking system for both optically tracking an object in three-dimensional space and transmitting control signals and/or data signals from the medical tracking system to the at least one medical appliance.

11. The method according to claim 10, wherein at least one of the at least one medical appliance is addressed using the infrared light source.

12. The method according to claim 10, wherein using the infrared light source includes outputting control signals and/ or data exchange signals in addition to or instead of tracking signal outputs of the infrared light source.

13. The method according to claim 10, further comprising controlling the camera array such that the camera array is not enabled to record positional data when tracking signal outputs are not generated.

14. The method according to claim 10, wherein control signals and/or data exchange signals during intervals between tracking signal outputs of the infrared light source.

15. The method according to claim 10, further comprising time displacing tracking signals for tracking an object relative to control signals for controlling the at least one medical appliance or data signals exchanged with the at least one medical appliance, wherein the tracking signals are different from the control signals and the data signals.

16. The method according to claim 10, wherein using includes using the infrared light source as a carrier for the control signals and/or the data signals transmitted between the medical tracking system and the at least one medical appliance.

17. The method according to claim 10, wherein using includes time-multiplexing light output by the light source into a plurality of time periods, wherein a first time period of the plurality of time periods corresponds to an image acquisition period of the camera array, and a second time period of the plurality of time periods corresponds to at least one of wireless control period or a data transfer period with the at least one medical appliance.

18. A computer program embodied on a non-transitory computer readable medium for controlling at least one medical appliance in a medical setting or for data exchange between the at least one medical appliance and other systems, said controlling and data exchange performed using medical tracking system that includes an infrared light source configured to provide infrared light in a medical workspace for reflection by passive markers placed in the medical workspace, comprising code that controls the infrared light source of the medical tracking system such that the infrared light source operates as a carrier for control signals and/or data signals communicated between the medical tracking system and the at least one medical appliance, wherein control of the infrared light source includes controlling the infrared light source to time-multiplex light output by the light source into a plurality of time periods, wherein a first time period of the plurality of time periods corresponds to an image acquisition period of a camera array, and a second time period of the plurality of time periods corresponds to at least one of a wireless control period or a data transfer period with the at least one medical appliance.

* * * * *